(12) United States Patent
Bogan, Jr. et al.

(10) Patent No.: US 6,740,620 B2
(45) Date of Patent: May 25, 2004

(54) SINGLE CRYSTALLINE PHASE CATALYST

(75) Inventors: Leonard Edward Bogan, Jr., Hatfield, PA (US); Daniel A. Bors, Maple Glen, PA (US); Fernando Antonio Pessoa Cavalcanti, Lafayette Hill, PA (US); Michael Bruce Clark, Jr., Coopersburg, PA (US); Anne Mae Gaffney, West Chester, PA (US); Scott Han, Lawrenceville, NJ (US)

(73) Assignee: Rohn and Haas Company, Philadelphia, PA (US)

(*) Notice: Subject to any disclaimer, the term of this patent is extended or adjusted under 35 U.S.C. 154(b) by 0 days.

(21) Appl. No.: 10/117,859

(22) Filed: Apr. 8, 2002

(65) Prior Publication Data

US 2002/0161256 A1 Oct. 31, 2002

Related U.S. Application Data

(60) Provisional application No. 60/286,235, filed on Apr. 25, 2001.

(51) Int. Cl.$^7$ ............. B01J 23/00; B01J 23/32; B01J 23/58; B01J 23/70; B01J 23/48
(52) U.S. Cl. ............. 502/300; 502/305; 502/306; 502/308; 502/311; 502/313; 502/317; 502/319; 502/321; 502/324; 502/325; 502/326; 502/328; 502/330; 502/332; 502/338; 502/339; 502/340; 502/341; 502/344; 502/347; 502/349; 502/353; 502/355
(58) Field of Search ................... 502/300–355

(56) References Cited

U.S. PATENT DOCUMENTS

| 4,678,657 A | 7/1987 | Sood et al. ............. 423/600 |
| 5,281,745 A | 1/1994 | Ushikubo et al. ......... 558/319 |
| 5,380,933 A | 1/1995 | Ushikubo et al. ......... 562/549 |
| 5,462,009 A | 10/1995 | Garrigus ............. 117/7 |
| 6,171,571 B1 | 1/2001 | Bedard et al. .......... 423/593 |
| 6,310,241 B1 * | 10/2001 | Karim et al. ............ 562/549 |
| 6,383,977 B1 * | 5/2002 | Karim et al. ............ 502/311 |
| 6,472,552 B1 * | 10/2002 | Bogan, Jr. ............ 558/319 |
| 6,504,053 B1 * | 1/2003 | Chaturvedi et al. ....... 562/549 |
| 2002/0183199 A1 * | 12/2002 | Bogan, Jr. ............ 502/215 |

FOREIGN PATENT DOCUMENTS

| EP | 0529853 A2 | 3/1993 |
| EP | 0 573 193 B1 | 12/1993 |
| EP | 1254707 A1 | 11/2002 |
| JP | 4-160007 A2 | 6/1992 |
| JP | 4-160008 A2 | 6/1992 |
| JP | 4-160009 A2 | 6/1992 |
| JP | 7-53448 | 2/1995 |
| JP | 7-078869 A2 | 3/1995 |
| JP | 9-118594 A2 | 5/1997 |

OTHER PUBLICATIONS

Translation of Japanese Laid–Open Patent Application Publication No. 6–228073 (Aug. 16, 1994).
Translation of Japanese Laid–Open Patent Application Publication No. 10–330343 (Dec. 15, 1998).
Translation of Japanese Laid–Open Patent Application Publication No. 11–43314 (Feb. 16, 1999).
Watanabe, et al., "New Synthesis Route For Mo–V–Nb–Te Mixed Oxides Catalyst For Propane Ammoxidation", Applied Catalysis A: General 194–195 (2000) 479–485. Jun. 1999.
Abstract of Ortega, et al., "Control Of Particle Morphology During Multicomponent Oxide Powder Generation By Spray Pyrolysis", J. Aerosol Sci. (1992), 23(Suppl. 1), S253–S256, no month avail.
Abstract of Hasegawa, et al., "Synthesis Of Monodispersed Complex Fine Particles Using Seed Particles From A Metal Alkoxide Method", Kagaku Kogaku (1996), (60)5, 319–320, no month avail.

* cited by examiner

Primary Examiner—Mark L. Bell
Assistant Examiner—Patricia L. Hailey
(74) Attorney, Agent, or Firm—Alan Holler; Marcella H. Bodner

(57) ABSTRACT

An orthorhombic phase mixed metal oxide is produced selectively in quantitative yield.

6 Claims, No Drawings

SINGLE CRYSTALLINE PHASE CATALYST

CROSS REFERENCE TO RELATED PATENT APPLICATION

This is a non-provisional application of prior pending U.S. provisional application serial No. 60/286,235 filed on Apr. 25, 2001.

The present invention relates to a catalyst for the oxidation of alkanes, or a mixture of alkanes and alkenes, to their corresponding unsaturated carboxylic acids by vapor phase catalytic oxidation and, more particularly, to a method of making the catalyst and to a process for the vapor phase catalytic oxidation of alkanes, or a mixture of alkanes and alkenes, to their corresponding unsaturated carboxylic acids using a catalyst prepared by the present method of making a catalyst. The present invention also relates to a process for the vapor phase catalytic oxidation of alkanes, or a mixture of alkanes and alkenes, in the presence of ammonia, to their corresponding unsaturated nitrites using a catalyst prepared by the present method of making a catalyst.

Nitrites, such as acrylonitrile and methacrylonitrile, have been industrially produced as important intermediates for the preparation of fibers, synthetic resins, synthetic rubbers, and the like. The most popular method for producing such nitrites is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula

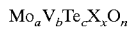

$Mo_aV_bTe_cX_xO_n$ wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula

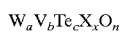

$W_aV_bTe_cX_xO_n$ wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships:
0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

The mixed metal oxide catalysts useful in the preparation of unsaturated carboxylic acids and unsaturated nitrites, as delineated above, can form more than one phase from the same starting materials under the same conditions. Often one phase performs better than the others, so it is desirable to prepare a catalyst that contains that phase exclusively, with the other phases substantially absent.

The aforementioned mixed metal oxide catalysts useful in the preparation of unsaturated carboxylic acids and unsaturated nitrites form at least three phases: a hexagonal phase (phase A), which is active but relatively unselective; an orthorhombic phase (phase B), which is active and selective; and a third phase (phase C) which is still poorly charterized. It is desirable to form the orthorhombic phase (phase B) selectively.

Two methods of forming the orthorhombic phase (phase B) with substantially reduced content of the hexagonal phase (phase A) are known. The first method involves the extraction of a mixed phase catalyst with a suitable solvent. In particular, Japanese Laid-Open Patent Application Publication No. 10-330343 discloses the washing of a mixed metal oxide of the formula $$Mo_aV_bSb_cX_xO_n$$

wherein X is at least one metal element selected from Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline earth metals, wherein, when a=1, $0.02 \leq b \leq 0.99$, $0.001 \leq c \leq 0.9$, $0 \leq x \leq 0.89$, $0.1 \leq c/b \leq 0.80$ and n is a value determined by the oxidation state of the other elements,
with a solvent selected from aqueous oxalic acid, ethylene glycol or aqueous hydrogen peroxide. The so-formed catalyst is used for the ammoxidation of alkanes to form nitriles. Japanese Laid-Open Patent Application Publication No. 11-043314 discloses the washing of a mixed metal oxide of the formula $$Mo_aV_bSb_cX_xO_n$$

wherein X is at least one metal element selected from Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline earth metals,
wherein, when a=1, $0.02 \leq b \leq 0.99$, $0.001 \leq c \leq 0.9$, $0 \leq x \leq 0.89$, $0.1 \leq c/b \leq 0.80$ and n is a value determined by the oxidation state of the other elements,
with at least one solvent selected from an aqueous solution of an organic acid, an alcohol, an aqueous solution of an inorganic acid or an aqueous solution of hydrogen peroxide. The so-formed material is indicated to be useful in such applications as electronic materials, electrode materials, mechanical inorganic materials and as catalysts in petrochemistry, etc. In particular, use as a catalyst in the oxidative dehydrogenation of ethane to produce ethylene is exemplified. While this methodology allows isolation of the orthorhombic phase, it is undesirable because about one-third of the original sample is lost in the extraction. The second method involves the hydrothermal synthesis of the catalyst precursor (Watanabe, et al., "New Synthesis Route for Mo—V—Nb—Te Mixed Oxides Catalyst for Propane Ammoxidation", Applied Catalysis A: General, Vol. 194-195, pgs. 479-485 (2000)). This gives, after calcination, a product enriched in the orthorhombic phase (phase B) but still containing the hexagonal phase (phase A).

It has now been found that the orthorhombic phase (phase B) can be prepared selectively, in quantitative yield, by seeding the catalyst precursor solution with orthorhombic phase (phase B) material.

Thus, in a first aspect, the present invention provides a novel catalyst component which consists of the orthorhombic phase of a mixed metal oxide of the formula $$A_aV_bN_cX_dO_e$$

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc and I,
wherein, when a=1, b=0.01 to 1, c=0.01 to 1, d=0.01 to 1 and e is dependent on the oxidation state of the other elements.

In a second aspect, the present invention provides a process for preparing an orthorhombic phase mixed metal oxide catalyst, said process comprising:

(a) admixing compounds of elements A, V, N and X and at least one solvent to form a first mixture,
wherein A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Ag, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc,
wherein A, V, N and X are present in such amounts that the atomic ratio of A:V:N:X is a:b:c:d, and
wherein, when a=1, b=0.01 to 1, c=0.01 to 1 and d=0.01 to 1;

(b) admixing a seeding effective amount of an orthorhombic phase mixed metal oxide, substantially free of hexagonal phase mixed metal oxide, with said first mixture to form a second mixture, (c) removing said at least one solvent from said second mixture to form a catalyst precursor; and (d) calcining said catalyst precursor to obtain said orthorhombic phase mixed metal oxide catalyst substantially free of hexagonal phase.

In a third aspect, the present invention provides a process for producing an unsaturated carboxylic acid, which comprises subjecting an alkane or a mixture of an alkane and an alkene to a vapor phase catalytic oxidation reaction in the presence of a catalyst produced by a process in accord with the present invention.

In a fourth aspect, the present invention provides a process for producing an unsaturated nitrile, which comprises subjecting an alkane, or a mixture of an alkane and an alkene, and ammonia to a vapor phase catalytic oxidation reaction in the presence of a catalyst produced by a process in accord with the present invention.

The mixed metal oxides prepared by the process of the present invention have the empirical formula $$A_aV_bN_cX_dO_e$$

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu and Sc and
wherein, when a=1, b=0.01 to 1.0, c=0.01 to 1.0, d=0.01 to 0.1 and e is dependent on the oxidation state of the other elements.

Preferably, when a=1, b=0.1 to 0.5, c=0.05 to 0.5 and d=0.01 to 0.5. More preferably, when a=1, b=0.15 to 0.45, c=0.05 to 0.45 and d=0.01 to 0.1. The value of e, i.e. the amount of oxygen present, is dependent on the oxidation state of the other elements in the catalyst. However, e is typically in the range of from 3 to 4.7.

The novel mixed metal oxides of the present invention have the empirical formula $$A_aV_bN_cX_dO_e$$

wherein A is at least one element selected from the group consisting of Mo and W, N is at least one element selected from the group consisting of Te and Se, and X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc and wherein, when a=1, b=0.01 to 1.0, c=0.01 to 1.0, d=0.01 to 0.1 and e is dependent on the oxidation state of the other elements.

Preferred mixed metal oxides have the empirical formulae $Mo_aV_bTe_cNb_dO_e$ or $W_aV_bTe_cNb_dO_e$ wherein a, b, c, d and e are as previously defined.

The orthorhombic phase mixed metal oxide substantially free of hexagonal phase may be prepared in the following manner.

In a first step, a solution may be formed by admixing compounds containing elements A, V, N and X, as previously defined, preferably at least one of which contains oxygen, and at least one solvent in appropriate amounts to form the solution.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, at the time of mixing.

For example, when a mixed metal oxide of the formula $Mo_aV_bTe_cNb_dO_e$ wherein the element A is Mo, the element N is Te and the element X is Nb, is to be prepared, an aqueous solution of niobium oxalate may be added to an aqueous solution of ammonium heptamolybdate, ammonium metavanadate and telluric acid, so that the atomic ratio of the respective metal elements would be in the prescribed proportions.

Once the aqueous solution has been formed, it may be seeded by the addition of a seeding effective amount of an orthorhombic phase mixed metal oxide seed which is substantially free of hexagonal phase mixed metal oxide. (By a seeding effective amount is meant an amount of seed material effective to cause nucleation of the orthorhombic phase, e.g., 0.01% by weight of seed material based on the total weight of the solution being seeded. By an orthorhombic phase mixed metal oxide which is substantially free of hexagonal phase mixed metal oxide is meant a material that contains not less than 90% by weight of orthorhombic phase based on the total weight of the material.) Such an orthorhombic phase mixed metal oxide seed substantially free of hexagonal phase mixed metal oxide may be obtained by any method known to the art.

Preferably, the orthorhombic phase mixed metal oxide substantially free of hexagonal phase mixed metal oxide to be used as seed may be prepared by:

taking a mixed metal oxide having the empirical formula

wherein A is at least one element selected from the group consisting of Mo and W, N is at least one element selected from the group consisting of Te, Se and Sb, and X is at least one element selected from the group consisting of Nb, Ta, Ti, Al Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc and wherein, when a=1, b=0.01 to 1.0, c=0.01 to 1.0, d=0.01 to 1.0 and e is dependent on the oxidation state of the other elements;

contacting the mixed metal oxide with a liquid contact member selected from the group consisting of organic acids, alcohols, inorganic acids and hydrogen peroxide to form a contact mixture; and recovering insoluble material, from the contact mixture, to obtain the orthorhombic phase mixed metal oxide seed substantially free of hexagonal phase mixed metal oxide.

Alternatively, the orthorhombic phase mixed metal oxide substantially free of hexagonal phase mixed metal oxide, to be used as seed, may be prepared by:

admixing compounds of elements A, V, N, X and at least one solvent to form a first mixture,
wherein A is at least one element selected from the group consisting of Mo and W, N is at least one element selected from the group consisting of Te, Se and Sb, and X is at least one element selected from the group consisting of Nb, Ta, Ti, Al Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc
wherein A, V, M and X are present in such amounts that the atomic ratio of A:V:N:X is a:b:c:d, and
wherein, when a=1, b=0.01 to 1.0, c=0.01 to 1.0 and d=0.01 to 1.0;

removing the at least one solvent from the first mixture to form a first precursor;

calcining the first precursor to form a first calcined precursor;

contacting the first calcined precursor with a liquid contact member selected from the group consisting of organic acids, alcohols, inorganic acids and hydrogen peroxide to form a contact mixture; and recovering insoluble material, from the contact mixture, to obtain the orthorhombic phase mixed metal oxide seed substantially free of hexagonal phase mixed metal oxide.

The contacting of the mixed metal oxide or the first calcined precursor with a liquid contact member selected from the group consisting of organic acids, alcohols, inorganic acids and hydrogen peroxide may be effected without any particular restrictions so long as the hexagonal phase (phase A) is substantially removed from the mixed metal oxide or the first calcined precursor. In this regard, the liquid contact member is normally used in an amount of 1 to 100 times the volume of the mixed metal oxide or the first calcined precursor, preferably 3 to 50 times the volume, more preferably 5 to 25 times the volume. Contacting at elevated temperatures will remove the hexagonal phase (phase B) more rapidly. However, if prolonged contact time is not a consideration, contacting at room temperature or below may be utilized. Normally, contact temperatures of room temperature to 100° C. are utilized, preferably 50° C. to 90° C., more preferably 60° C. to 80° C. As previously noted, contact time will be affected by the temperature at which the contacting is carried out. Normally, contact times of 1 to 100 hours are utilized, preferably 2 to 20 hours, more preferably 5 to 10 hours. The contact mixture is preferably agitated during the contacting.

There are no particular restrictions upon the organic acids which may be used as the liquid contacting member. For example, oxalic acid, formic acid, acetic acid, citric acid and tartaric acid may be used, however, oxalic acid is preferred. If the organic acid is a liquid, it may be used as is or in an aqueous solution. If the organic acid is a solid, it is used in an aqueous solution. When using aqueous solutions, there are no particular restrictions on the concentration of the organic acid. Normally, the concentration of the organic acid in the aqueous solution can vary from 0.1 to 50% by weight, preferably 1 to 15% by weight.

There are no particular restrictions upon the alcohols which may be used as the liquid contacting member. For example, methanol, ethanol, propanol, butanol, hexanol and diols may be utilized, however, alcohols having one to four carbon atoms are preferred, with ethylene glycol being particularly preferred. The alcohols may be utilized in the form of aqueous solutions, but, if so, the water content should be held to 20% by weight or less for the best effectiveness.

Similarly, there are no particular restrictions upon the inorganic acids which may be used as the liquid contacting member. For example, nitric acid, sulfuric acid, phosphoric acid, hydrochloric acid, perchloric acid, chloric acid and hypochlorous acid may be used, however, the use of nitric acid is especially preferrred. The inorganic acids are typically used as aqueous solutions with concentrations of the acids in the range of from 0.1 to 50% by weight, preferably from 0.1 to 10% by weight.

When hydrogen peroxide is utilized as the liquid contacting member, it is used in the form of an aqueous solution having a concentration in the range of from 0.1 to 50% by weight, preferably from 1 to 10% by weight.

After contacting with the liquid contacting member, insoluble material is recovered from the so-formed contact mixture for use as seed material. The insoluble material may be recovered by any conventional liquid-solid separation method, e.g., centrifugation or filtration. If the contacting was conducted at elevated temperature, the contact mixture may be cooled prior to recovery of the insoluble material.

After the solution has been seeded, the solvent is removed by any suitable method, known in the art, to form a catalyst precursor. Such methods include, without limitation, vacuum drying, freeze drying, spray drying, rotary evaporation and air drying.

For example, in the case of water being the solvent: Vacuum drying is generally performed at pressures ranging from 10 mmHg to 500 mmHg. Freeze drying typically entails freezing the solution, using, for instance, liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° C. to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. (The calcination conditions disclosed hereinafter may also be used in the formation of the seed material as set forth above.) The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 650° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In one mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

In a particularly preferred mode of operation, the catalyst precursor in the first stage of calcination is placed in a desired flowing oxidizing atmosphere at room temperature and then raised to the first stage calcination temperature, at a rate of from 1° C./min to 20° C./min, preferably 2°/min to 10° C./min. It is then held at the first stage calcination temperature, in the desired flowing oxidizing atmosphere, for the desired first stage calcination time. After the desired first stage calcination time has passed, the atmosphere is replaced with a desired flowing non-oxidizing atmosphere, preferably while maintaining the temperature at the first stage calcination temperature; the temperature is then raised to the desired second stage calcination temperature at a rate of from 1° C./min to 20° C./min, preferably 2° C./min to 10° C./min. It is then held at the second stage calcination temperature, in the desired flowing non-oxidizing atmosphere, for the desired second stage calcination time.

With calcination, a catalyst is formed having the formula $A_aV_bN_cX_dO_e$ wherein A, N, X, O, a, b, c, d and e are as previously defined.

The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the mixed metal oxide may be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals, after being seeded with the orthorhombic phase mixed metal oxide material, are contacted with the dry support such that the support is wetted; then, the resultant wetted material is dried, for example, at a temperature from room temperature to 200° C. followed by calcination as described above.

In a third aspect, the present invention provides a process for producing an unsaturated carboxylic acid, which comprises subjecting an alkane, or a mixture of an alkane and an alkene, to a vapor phase catalytic oxidation reaction in the presence of a catalyst produced in accord with the present invention to produce an unsaturated carboxylic acid.

In the production of such an unsaturated carboxylic acid, it is preferred to employ a starting material gas which contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{3-8}$alkane and $C_{3-8}$alkene, particularly propane and propene, isobutane and isobutene or n-butane and n-butene.

As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

This third aspect of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In a fourth aspect, the present invention provides a process for producing an unsaturated nitrile, which comprises subjecting an alkane, or a mixture of an alkane and an alkene, to a vapor phase catalytic oxidation reaction with ammonia in the presence of a catalyst produced in accord with the present invention to produce an unsaturated nitrile.

In the production of such an unsaturated nitrile, as the starting material alkane, it is preferred to employ a $C_{3-8}$alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is preferred to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitrites to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

This fourth aspect of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The processes of these still further aspects of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

COMPARATIVE EXAMPLE 1

A Mo—V—Te—Nb mixed metal oxide (56.60 g) was added to a solution of 23.3 g oxalic acid dihydrate in 215 g water and stirred 6 hrs at 70–80° C. It was cooled, filtered and dried to yield 45.28 g black solid. The X-ray diffraction pattern for this sample showed significant intensity at 2θ (2 theta) values of 28.3° and 36.2°, indicative of the hexagonal phase.

EXAMPLE 1

Ammonium heptamolybdate tetrahydrate (17.03 g), ammonium metavanadate (3.35 g) and telluric acid (5.09 g) were dissolved in 284 g water with heating. The resulting orange solution was cooled to 40° C. Oxalic acid dihydrate (0.97 g) was dissolved in a 6.5 weight percent solution of niobium oxalate in water (99.33 g). The so-formed niobium solution was added to the orange solution and then 100 mg of the material as prepared in Comparative Example 1 was added to the combined solutions. The mixture was dried, first on a rotary evaporator, and then overnight, under vacuum (6 mbar). The resulting precursor was sieved to remove >50 mesh fines, then calcined in a flowing atmosphere as follows: in an air atmosphere, the precursor was heated from room temperature to 275° at a rate of 10° C./min and then held at 275° C. for 1 hr; the atmosphere was switched to argon; in an argon atmosphere, the precursor was heated from 275° C. to 600° C. at a rate of 2° C./min and then held at 600° C. for 2 hrs. The X-ray diffraction pattern for this sample showed very little intensity at 2θ (2 theta) values of 28.3° and 36.2°, indicative of a lack of the hexagonal phase.

What is claimed is:

1. A process for preparing an orthorhombic phase mixed metal oxide catalyst, said process comprising:
   (a) admixing compounds of elements A, V, N and X and at least one solvent to form a solution, wherein A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy Ho Er, Tm, Yb, Lu, Au, Ag, Re, Pr, Zn, Ga, Pd, Ir, Nd, Y, Sm, Tb, Br, Cu, and Sc wherein A, V, N and X are present in such amounts that the atomic ratio of A:V:N:X is a:b:c:d, and wherein, when a=1, b=0.01 to 1, c=0.01 to 1 and d=0.01 to 1;
   (b) admixing a seeding effective amount of an orthorhombic phase mixed metal oxide seed, substantially free of hexagonal phase mixed metal oxide, with said solution to form a seeded solution,
   (c) removing said at least one solvent from said seeded solution to form a catalyst precursor; and
   (d) calcining said catalyst precursor to obtain said orthorhombic phase mixed metal oxide catalyst.

2. The process for preparing an orthorhombic phase mixed metal oxide catalyst according to claim 1, wherein N is at least one element selected from the group consisting of Te and Sc.

3. The process for preparing an orthorhombic phase mixed metal oxide catalyst according to claim 1, said orthorhombic phase mixed metal oxide seed, substantially free of hexagonal phase mixed metal oxide, is prepared by the process comprising:
   (i) providing a mixed metal oxide having the empirical formula

wherein A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc wherein, when a =1,b=0.01 to 1, c=0.01 to 1, d=0.01 to 1 and e is dependent on the oxidation state of the other elements;
   (ii) contacting said mixed metal oxide with a liquid contact member selected from the group consisting of organic acids, alcohols, inorganic acids and hydrogen peroxide to form a contact mixture; and
   (iii) recovering insoluble material from said contact mixture to obtain said orthorhombic phase mixed metal oxide seed substantially free of hexagonal phase mixed metal oxide.

4. The process for preparing an orthorhombic phase mixed metal oxide catalyst according to claim 3, wherein said liquid contact member is an aqueous solution of oxalic acid.

5. The process for preparing an orthorhombic phase mixed metal oxide catalyst according to claim 1, wherein said orthorhombic phase mixed metal oxide seed, substantially free of hexagonal phase mixed metal oxide, is prepared by the process comprising:
   (a) admixing compounds of elements A, V, N and X and at least one solvent to form a first mixture, wherein A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb, Lu, Au, Ag, Re, Pr, Zn, Ga, Pd, Ir, Nd, Y, Sm, Tb, Br, Cu, and Sc wherein A, V, N and X are present in such amounts that the atomic ratio of A:V:N:X is a:b:c:d, and wherein, when a=1, 0.01 to 1, c 0.01 to l and d0.01 to 1;
   (b) removing said at least one solvent from said first mixture to form a first precursor;
   (c) calcining said first precursor to form a first calcined precursor;
   (d) contacting said first calcined precursor with a liquid contact member selected from the group consisting of organic acids, alcohols, inorganic acids and hydrogen peroxide to form a contact mixture; and
   (e) recovering insoluble material from said contact mixture to obtain said orthorhombic phase mixed metal oxide seed, substantially free of hexagonal phase mixed meta oxide.

6. The process for preparing an orthorhombic phase mixed metal oxide catalyst according to claim 5, wherein said liquid contact member is an aqueous solution of oxalic acid.

* * * * *